United States Patent [19]

Bonfield et al.

[11] 4,349,520
[45] Sep. 14, 1982

[54] CONTINUOUS HYDROLYSIS OF KETOXIME

[75] Inventors: John H. Bonfield, Basking Ridge; Stylianos Sifniades, Madison; Harry E. Ulmer, Morris Township, Morris County, all of N.J.

[73] Assignee: Allied Corporation, Morris Township, Morris County, N.J.

[21] Appl. No.: 295,347

[22] Filed: Aug. 24, 1981

[51] Int. Cl.³ ............................................. C01B 21/14
[52] U.S. Cl. .................................. 423/387; 423/388; 568/338; 568/383
[58] Field of Search ................ 423/387, 388; 568/338, 568/383

[56] References Cited

U.S. PATENT DOCUMENTS 2,414,142  1/1947  Dreyfus ............................... 423/387
3,105,741  10/1963  Moore et al. ......................... 423/387

FOREIGN PATENT DOCUMENTS 1043297  11/1958  Fed. Rep. of Germany ...... 423/387
46-2413  1/1971  Japan .................................... 423/387

Primary Examiner—O. R. Vertiz
Assistant Examiner—Wayne A. Langel
Attorney, Agent, or Firm—Alan M. Doernberg; Gerhard H. Fuchs

[57] ABSTRACT

A mixture of ketoxime such as methyl ethyl ketone oxime (MEKO), an inorganic acid such as sulfuric acid and optionally water is fed to an intermediate point of a fractional distillation column. Steam is fed to the base of the column and operating conditions are sufficient to produce the corresponding ketone (e.g. methyl ethyl ketone) or its water azeotrope as the overhead product and the corresponding hydroxylammonium salt (e.g. the sulfate) as the bottoms. Crystallization of the salt from the bottoms leaves a mother liquor which may be recycled to a reboiler from which the steam is generated.

13 Claims, 1 Drawing Figure

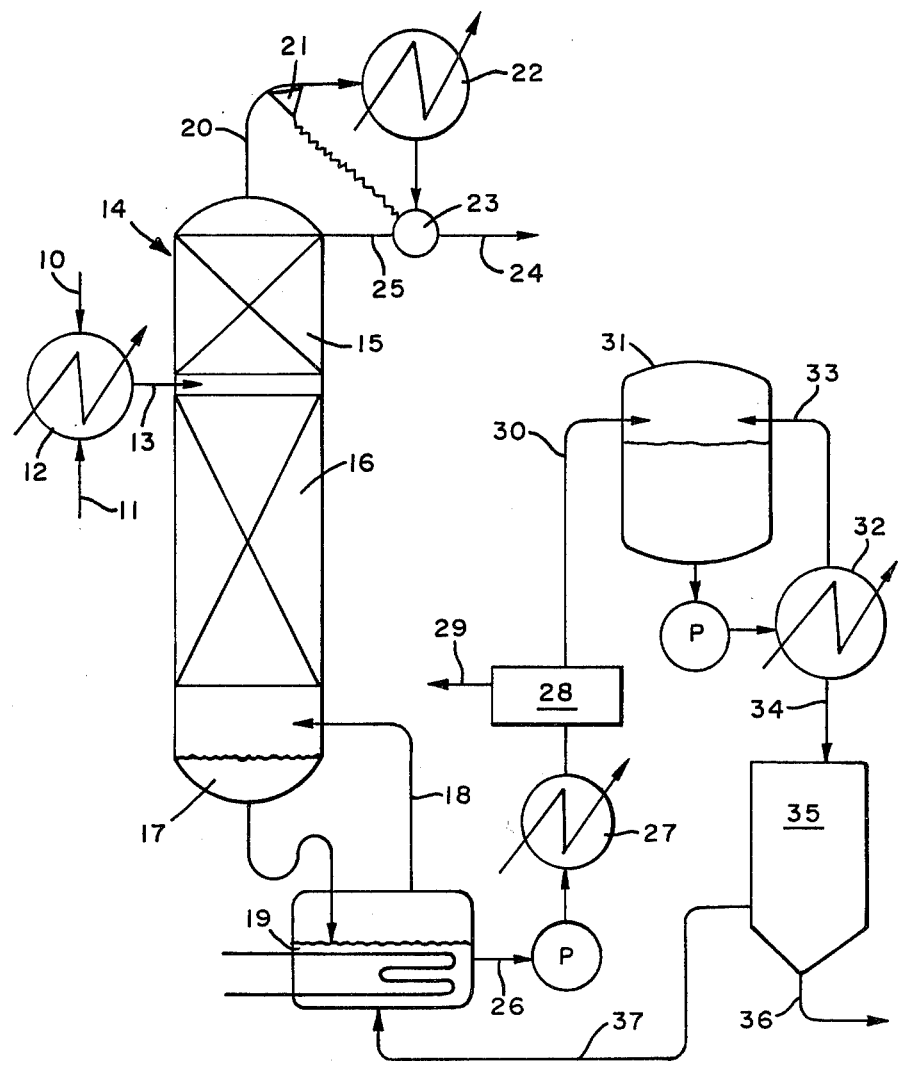

CONTINUOUS HYDROLYSIS OF KETOXIME

DESCRIPTION

BACKGROUND OF THE INVENTION

The present invention relates to a process for the hydrolysis of ketoximes such as acetone oxime or methyl ethyl ketone oxime, and particular to the continuous acid hydrolysis of such ketoximes.

It has been proposed in U.S. Pat. No. 3,105,741 to Moore, Jr. et al. (1963) to produce concentrated acqueous solutions of hydroxylamine or hydroxylammonium salts from dilute aqueous solutions of such salts in a mixture with ammonium salts. A methyl ketone such as 2-octanone or 2-heptanone is reacted with the dilute solutions to form the corresponding oxime. The oxime is then phase separated in a countercurrent fashion from the dilute aqueous solution. The oxime is then hydrolyzed with relatively concentrated aqueous acid to reform the methyl ketone, which is then phase separated off leaving a concentrated salt solution. The methyl ketone is recycled to the oximation and the concentrated solution is evaporatively crystallized.

Japanese U.S. Pat. No. 7,102,413-R describes producing hydroxylammonium chloride of high purity by hydrolyzing methyl ethyl ketone oxime with aqueous hydrochloric acid of less than 20 weight percent HCl. The methyl ethyl ketone is distilled off, and the liquid then concentrated into crude crystals which are recrystallized with methanol. Other similar references are described in the background section of the Moore, Jr. et al. patent, with particular reference to U.S. Pat. No. 2,414,142 and the Journal of the American Chemistry Society, vol. 45, page 188 (1923).

While such processes are effective to produce concentrated hydroxylammonium salts from aqueous solutions via ketoximes, they require extensive amounts of equipment for serially oximating, phase separating, hydrolyzing and distilling off the ketone. Because of the apparently large reaction times required, substantial inventories, particular of ketone and ketoxime, would be required to practice the process.

BRIEF DESCRIPTION OF THE INVENTION

The present invention includes a process for the continuous hydrolysis of a ketoxime which comprises the steps:

(a) feeding to a fractional distillation column at an intermediate feed point a feed mixture comprising an aliphatic or cycloaliphatic ketoxime of 3–8 carbons and an inorganic acid which is not strongly oxidizing;

(b) feeding steam adjacent the base of said column;

(c) operating said column with sufficient steam feed, sufficient effective plates between said feed point and the base of the column and sufficient reflux to hydrolyze said ketoxime in said column and form the ketone corresponding to said ketoxime and the hydroxylammonium salt of said inorganic acid;

(d) recovering an overheat comprising said ketone; and (e) recovering as bottoms an aqueous solution comprising said hydroxylammonium salt.

BRIEF DESCRIPTION OF THE DRAWING

FIG. 1 is a schematic view of an embodiment of the hydrolysis process of the present invention, together with steps for crystallization of the product hydroxylammonium salt and recycle of the mother liquor.

DETAILED DESCRIPTION OF THE INVENTION

The hydrolysis process of the present invention is practiced in a column, preferably with continuous feed of reactants and steam. Any type of conventional fractional distillation column may be used, with both tray and packed columns being suitable. The column should have an upper section for distillation of product ketone and a lower section for hydrolysis, with the reactant ketoxime mixed with the reactant acid introduced between the two sections.

The ketoxime hydrolyzed in the present process may be an aliphatic or cycloaliphatic ketoxime of 3-8 carbons such as acetone oxime, methyl ethyl ketone oxime, 2-hexanone oxime, 2-octanone oxime, 4-octanone oxime, cyclohexanone oxime, methylcyclohexanone oxime, ethylcyclohexanone oxime, or other similar materials. The ketone product of hydrolysis (or its water azeotrope) must have a lower boiling point (or conversely a higher vapor pressure at the same temperature) than the corresponding ketoxime (or its water azeotrope). The preferred ketoximes are those of 3–4 carbons: acetone oxime and methyl ethyl ketone oxime.

The inorganic acid employed is one which is not strongly oxidizing. The preferred acids are sulfuric, hydrochloric acid and phosphoric acid, but other suitable inorganic acids may be used. Nitric acid (an oxidizing acid) is unsuitable because, under the hydrolysis conditions, the product hydroxylammonium nitrate is unstable. Other acids, such as perchloric acid, which are similarly highly oxidizing are also unsuitable. Mildly oxidizing acids such as sulfuric acid may be employed.

The ketoxime and the acid are fed together into the column as a mixture, which mixture may also include some water. It is undesirable to feed a strong acid directly to the column since, in the column, the product ketone will degrade if contacted by unneutralized strong acid. In the case of sulfuric acid, acid not neutralized by premixing with the ketoxime should not come into contact with ketones such as acetone, methyl ethyl ketone or cyclohexanone. Partially neutralized acid, such that the first proton of each sulfuric acid is neutralized by ketoxime, can be fed to the column, since the second proton is not acidic enough to cause ketone degradation. In the case of hydrochloric acid complete neutralization is desirable. In the case of phosphoric acid, at least the first of the three protons should be neutralized. Conveniently, the entire stoichiometric amount of ketoxime to completely neutralize all of the protons of the acid may be introduced with the acid. It is contemplated that when less than the stoichiometric amount of ketoxime is introduced with the acid, a separate feed of ketoxime may be introduced adjacent the feed point or below the main feed point, with the total ketoxime introduced approximately corresponding to the stoichiometric amount.

When the water balance permits, it is desirable to introduce some water with the ketoxime in the acid to prevent the Beckmann rearrangement of the ketoxime by very strong acid. In the examples below, this is accomplished by using sulfuric acid of 60–70 weight percent concentration. The exact amount of water introduced with the feed mixture, compared to introduction elsewhere, is not critical; the amounts can be adjusted with a view towards balancing the avoidance of Beckmann rearrangement (by introducing enough water with the feed mixture) against maximizing hydrolysis rate (by keeping water levels in the column adjacent the feed point as low as feasible) and also with a view towards controlling process water balance. Normally the feed mixture will be essentially free of materials other than the inorganic acid, the ketoxime, water and impurities normally present in these materials. In the mixture, the ketoxime and the inorganic acid normally form salts or other complexes. When the feed mixture is made up, cooling is normally desirable so that the temperature of the feed mixture corresponds to the temperature at the feed point with a normal temperature profile in column from the base where steam is introduced to the top of the column, which has a temperature corresponding to the boiling point at the operating pressure of either the ketone or of the ketone-water azeotrope that is being generated.

In feeding steam to the base of the column, it is preferred that such steam be generated by reboiling the aqueous hydroxylammonium salt solution which is the bottoms product. As is illustrated below, it is further desirable to recirculate mother liquor from recrystallization of such aqueous salts and to reboil the combination of recirculating salt solution and mother liquor. Steam may be introduced from a reboiler to the column as illustrated in FIG. 1, or other conventional reboiler techniques can be used involving recirculation of bottoms into the base of the column with steam then generated from the base of the column upward to the bottom tray or packing.

Various operating conditions are adjusted to attain essentially complete hydrolysis of the ketoxime in the lower section of the column and the desired degree of purification of the ketone in the upper section of the column. As is described in Examples 6 and 7 below, one critical parameter is the rate of steam fed to the base of the column. For any particular column, with a particular diameter, number of effective trays below the feed point and feed rate, a specific ratio of steam feed to ketoxime feed will be required to achieve a particular desired conversion of ketoxime to ketone and hydroxylammonium salts in the column. For example, with a 20 tray column, at least about three units of steam, and preferably between about 4 and about 5 units of steam, per units of sulfuric acid fed expressed as hydroxylammonium sulfate, are required to achieve 95 percent hydrolysis of methyl ethyl ketone oxime. In a sense, steam boil-up rate may be a control upon the mass transfer of the ketone upward through the column and upon the reflux ratio. The particular steam ratios required for a particular column under particular circumstances can be easily determined as indicated in Examples 6 and 7, or by supplementation thereof with routine experimentation. The amount of steam that can be fed to the base of a column without flooding of the column will operate as one limitation upon the capacity of the column for the present reaction.

A second parameter which is significant to achieving the desired hydrolysis conversion rate is the number of effective plates between the feed point and the base of the column where steam is fed. By number of effective trays is meant the conventional engineering criteria for a column, whether tray, packed or other configuration, with respect to distillation capacity of the column being equivalent to a fixed number of theoretical trays, each operating at 100% efficiency.

The third criteria which should be sufficient to achieve complete conversion is the reflux of the column. While in normal operation, the reflux ratio will be that necessary to achieve the desired separation and purification of the ketone above the feed point, some minimum amount of reflux is generally required to prevent unreacted ketoxime from escaping to any large extent upwards from the feed point and thus being removed as overheads without being hydrolyzed.

In practicing the present process, the overheads which are removed contain the ketone and, depending on the individual ketone, may also contain an azeotropic amount of water. Normally, the reflux ratio and number of effective trays above the feed point are sufficient to lower the water concentration either to minor amounts in the case of ketones (e.g., acetone) which do not form water azeotropes and to a level corresponding to the ketone-water azeotrope for ketones (e.g., methyl ethyl ketone) which do form ketone-water azeotropes. It is preferred to operate the column in a manner that minimizes the presence of materials other than ketone and water in the overhead that is finally removed. One preferred method of accomplishing this result is to monitor the temperature of the overheads continuously. When the overheads temperature exceeds the boiling point of the ketone (or its water azeotrope) at the operating pressure under equilibrium conditions by more than a predetermined level (e.g. 1° or 2° C.) the column operation reverts to total reflux. Whenever the temperature of the overheads is less than the predetermined level above such boiling point, the column is operated at partial reflux, with the remainder of the overheads being removed as ketone or ketone-water azeotrope.

It should be appreciated, however, that when the present process is employed as part of the cyclical process to produce concentrated hydroxylammonium salts from dilute hydroxylammonium salts by oximation and then hydrolysis, the presence of some ketoxime in the overheads can be tolerated. In such case, the ketoxime in the overheads is returned with the ketone to the oximation step, where the remainder of the ketone is converted back to ketoxime and returned as feed mixture back to the column. A small amount of ketoxime in the overheads, as a proportion of ketone, has only a minor impact upon the overall capacity of the system and, under certain conditions, permits the system to operate either with fewer effective trays above the feed mixture or lower reflux ratios, or both. This may result either in more efficient operation, more capacity for a given column or a reduction in capital cost of the column.

The bottoms from the column are an aqueous solution comprising the hydroxylammonium salt corresponding to the inorganic acid fed in the feed mixture (provided that at least a stoichiometric amount of oxime was fed). Preferably, when stoichiometric ratios are used, the hydroxylammonium salt will have the maximum effective hydroxylamine concentration by having all protons of the acid neutralized by the hydroxylammonium cation. This corresponds to one hydroxylammonium cation for hydrochloric acid, two for sulfuric acid and three for phosphoric acid. It is contemplated to have some ketoxime remaining in the aqueous solution as it falls from the lowest tray or packing of the column, but preferably at least 90 percent and more preferably 95 percent of the ketoxime is hydrolyzed before leaving the column. Some further hydrolysis may occur in the reboiler or in the recirculation of bottoms liquid between the base of the column and a forced circulation reboiler. For effective operation, it is preferable that the hydroxylammonium salt have a predetermined concentration in the aqueous solution formed at the base of the column. In the case of hydroxylammonium sulfate this concentration is between about 20 and about 40 weight percent, preferably between about 25 and about 30 weight percent. It should be appreciated these concentrations refer to liquid leaving the base of the column, and this concentration may be somewhat different in the reboiler because of recirculation of mother liquor from crystallization or other factors.

The aqueous solution removed as bottoms from the column has a temperature of approximately 100°–110° C. such that the steam fed to the base of the column is boiled from this mixture. A portion of the mixture is preferably filtered to remove any sludge by-products, phase separated (if any separate phase of oxime is present) and then crystallized to recover the hydroxylammonium salts as a solid. It is preferable that the bottoms taken from the reboiler have a concentration which does not cause crystallization during transit from the reboiler through the filter to the crystallizer. In the case of hydroxylammonium sulfate, when this concentration does not exceed 40-45 weight percent, crystallization does not occur so long as the liquid is maintained at a temperature of at least 30° C. Higher concentrations may be used, but then it is desirable to heat the pipes through which the hydroxylammonium salts pass to prevent crystallization.

Any conventional crystallization system can be used, such as a refrigeration cooled tank or a crystallization vessel with slurry pumped from the bottom through a refrigeration coil and back into the vessel. The latter system is generally preferred, at least in the case of salts such as hydroxylammonium sulfate which can form large crystals, since pumping from the bottom of the vessel improves crystallization in manageably sized particles. A portion of the slurry can be withdrawn, either continuously or in a batch fashion, from the crystallization system, and solids separated from the liquid in a conventional fashion, such as centrifugation, filtration, decantation or other similar techniques. The liquid, conventionally referred to as mother liquor, is then preferably recirculated to the reboiler or otherwise mixed with the aqueous solution falling from the base of the column. If, after extensive reuse of the aqueous solution, some build up of by-products is detected, a purge of some or all of the mother liquor can be made, with the used mother liquor being suitable for the oximation of various aldehydes or ketones which are distilled from the oximation reaction mixture, leaving the impurities in the remaining solution.

DESCRIPTION OF THE PREFERRED EMBODIMENTS

A preferred mode of practicing the present process employing methyl ethyl ketoxime and sulfuric acid is illustrated in FIG. 1 and described herein. Suitable modifications can be made as described previously, and within the broad scope of the invention as described in the claims that follow the description of FIG. 1 and the examples.

In FIG. 1, a ketoxime stream 10 containing a ketoxime such as methyl ethyl ketone oxime and an aqueous acid stream 11, such as 60–70 weight percent of sulfuric acid, are together fed to a cooler-mixer 12. Water or other cooling means is passed in heat exchange with the cooler mixer 12 so as to remove the heat of mixing and produce a feed mixture 13 which is then fed to an intermediate feed point in column 14.

Column 14 contains packing or trays in two sections, an upper section 15 above the feed point and a lower section 16 below the feed point. A representative column contains 10 trays in section 15 and 20 trays in section 16, but other column sizes, packing materials and the like may be employed in similar fashion. A liquid 17 is collected at the base of the column and withdrawn into a reboiler. Steam is returned from the reboiler in stream 18 to the column above liquid 17 but below the base of the column.

Liquid 19 is maintained as inventory in the reboiler in sufficient amount to minimize foaming as steam is generated and to maintain a relatively stable concentration of materials in the reboiler as liquid is returned from the column and mother liquor is recirculated as described below. With suitable operating conditions as described previously, section 16 will operate to hydrolyze the ketoxime fed in feed mixture 13 such that at least 95 and preferably about 97 percent of the ketoxime is hydrolyzed. A representative composition for liquid 17 is 25–35 weight percent hydroxylammonium sulfate, a slight amount of methyl ethyl ketone oxime and the balance water. The methyl ethyl ketone oxime present would represent 1–5% of that fed in stream 10.

The ketone methyl ethyl ketone will distill upward from lower section 16 to upper distillation section 15 as it is formed. In section 15 the ketone azeotrope (88 percent methyl ethyl ketone, 12 percent water by weight at atmospheric pressure) will be fractionated away from the methyl ethyl ketone oxime azeotrope (0.15 weight percent oxime at atmospheric pressure). The ketone azeotrope will be removed from the column as overheads in stream 20. The temperature of overheads 20 is sensed by a sensor 21. The overheads are then condensed in condensor 22 and fed to a reflux splitter 23 operationally controlled by sensor 21. During normal operation, when the temperature sensed by element 21 corresponds to the azeotrope or is 0.5° C. or 1° C. higher than the azeotrope boiling point, a portion of the condensed overheads will be fed forward in stream 24 and returned to the oximator in a system for continuous oximation and hydrolysis. The remainder of the condensed overheads are returned in stream 25 to the top of the column. As is conventional, the ratio of material in stream 25 to material in stream 24 is termed the reflux ratio. When the temperature sensed by sensor 21 exceeds the boiling point of the azeotrope by a predetermined amount (e.g., 1° C.) reflux splitter 23 reverts to complete reflux, with all of the condensed overheads returned in stream 25. Since the increase in temperature would be caused by removing ketone-water azeotrope more rapidly than it is being formed, complete reflux will lower the operating temperature through column section, 15 as the inventory of ketone increases. Once the inventory is sufficient to restore the azeotropic composition, the temperature sensed by sensor 21 will become sufficiently low for reflux splitter 23 to resume partial reflux operation.

A stream of the liquid 19 in the reboiler is pumped in stream 26 through a cooler, where it is cooled from 100°–110° C. of the reboiler to a normal temperature such as 40°–60° C. and filtered through filter 28 to remove any by-products. The by-products may be recovered or removed by periodically changing filter material, with stream 29 in FIG. 1 representing this by-product removal. If ketoxime is present in the liquid 19, it will form a separate phase and can be removed on a continuous or purge basis anywhere in the recirculating system, but preferably immediately downstream of the filter 28. The filtrate is then fed in stream 30 to a conventional crystallizer vessel 31 from which material is withdrawn from the bottom and pumped through a refrigeration-cooled heat exchanger 32 and returned in stream 33 to the crystallizer. Either continuously or periodically, a portion or all of the slurry passing through heat exchanger 32 may be conducted in stream 34 to a centrifuge 35 or other conventional liquid-solid separation device. From the centrifuge 35 the solids are removed in the stream 36 and, depending upon the desired use, dried or otherwise treated and subsequently packaged. The mother liquor from centrifuge 35 is fed in stream 37 back to the reboiler so as to mix with liquid 17 to form reboiler inventory liquid 19.

Representative operating conditions for such a column 14 with a 10 tray section 15 and a 20 tray section 16 are 6:1 reflux ratio, 25–35 weight percent hydroxylammonium sulfate in liquid 17, 40–42 weight percent hydroxylammonium sulfate in reboiler inventory 19, 74° C. overheads temperature and 103°–105° C. reboiler temperature. In such a mode of operation, a crystallizer 31 operating at 0°–5° C. will cause the mother liquor in stream 37 to have a hydroxylamine sulfate concentration of about 30–31 weight percent, with the excess of the concentration of liquid 19 over that of the mother liquor removed as solids in stream 36. As illustrated in the examples that follow, such a system may be operated with the mother liquor recycled a large number of time without the formation of by-products in significant amounts.

EXAMPLES

EXAMPLE 1

A feed solution was prepared by adding 102 g 96 weight % $H_2SO_4$ (1 mol) to 300 g ice and then adding with agitation 174 g (2 mol) methyl ethyl ketone oxime (MEKO). Solution density at 20° C. was 1.176. This solution was then continuously fed to the 15th plate of a 25 plate nominal one inch (2.5 cm) Oldershaw column in which steam boil up has been previously established while on total reflux. Feed rate was 5.16 mL (6.06 g/min). After a short while the head temperature, initially at 100° C., dropped to 74° C., the reboiler to 103° C. and the feed plate to 95° C. At 74° C. head temperature MEK-$H_2O$ azeotrope was continuously withdrawn at 3:1 reflux ratio, with heads reverting to total reflux at 76° C. After one hour, the bottoms of the column assayed at 94% hydrolysis, reboiler outflow (reboiler inventory 100 mL) 97% hydrolysis. $(NH_2OH)_2H_2SO_4$ at outflow was 40.2 weight %. During a timed run period over which 576 g of feed was fed, 194 mL (164 g) of overheads was collected which assayed 85 weight % methyl ethyl ketone (MEK), 0.4 weight % MEKO, balance water. Effluent from reboiler assayed 159.1 g $(NH_2OH)_2H_2SO_4$, 2.9 g $H_2SO_4$, balance water. $(NH_2OH)_2H_2SO_4$ was 39.5 weight %. Column bottoms were 32 weight % $(NH_2OH)_2H_2SO_4$.

EXAMPLE 2

The run as in example 1 was continued with heat input to reboiler being increased such that $(NH_2OH)_2H_2SO_4$ in column bottoms was 25 weight %. At this condition 97–98% hydrolysis was attained on the column.

EXAMPLE 3

The run as in example 1 but feeding to the fifth plate of a 15 plate column. Hydrolysis at column bottom was 80%, out of reboiler 85%.

COMPARATIVE EXAMPLE 4

The run as in example 1 but feeding directly to the reboiler topped with (now) a 5 plate column. Reboiler outflow showed only 47% hydrolysis.

EXAMPLE 5

A continuous packed column was set up. The hydrolysis section was 38" of ¼" glass helix packing in a one inch (2.5 cm) nominal inside diameter Oldershaw column. The MEK fractionation section was 20 inches (0.51 m) of the same packing. The reboiler had 250 mL inventory volume. After initial water boil-up from an initial charge of 30 weight % $(NH_2OH)_2H_2SO_4$ solution was established, MEKO and 95 weight % $H_2SO_4$ with premix and precool and were fed continuously at a rate of 4 mL/min (3.68 g/min) and 1.12 mL/min (2.06 g/min) respectively. The 30 weight % $(NH_2OH)_2H_2SO_4$ feed (initial) rate to the reboiler was varyed from 70 to 160 mL/min to control the $(NH_2OH)_2H_2SO_4$ in the reboiler effluent in the 40–50 weight % range. MEK takeoff was controlled as in example 1. Operation was continued in this manner with reboiler effluent being withdrawn, upper organic phase separated (75 weight % MEKO) and returned to feed MEKO, cooled to 10°–15° C., mother liquor (32–34 weight % $(NH_2OH)_2H_2SO_4$) then being recycled to reboiler as above and the whole cycle repeated.

In this run column bottoms assayed 97–98% hydrolysis, 20–25 weight % $(NH_2OH)_2H_2SO_4$. Reboiler outflow varied (depending on ML recycle rate) 40–55 weight % $(NH_2OH)_2H_2SO_4$ and 97–98% hydrolysis. Crystallization recovered $(NH_2OH)_2H_2SO_4$ was white, and assayed 99.5% pure. The MEKO phase separated from the reboiler effluent became progressively more yellow, but never did need to be purged from the process.

EXAMPLE 6

Mixtures of MEKO, 96% sulfuric acid and water (MEKO: $H_2SO_4$ ratios about 2.05 to 2.10) were fed at five different rates to the 20th tray of the 30 tray Oldershaw column used in the previous examples having a two inch (51 mm) nominal inside diameter. The column was operated at a 4:1 reflux ratio except when the heads temperature exceeded 75° C. (it then reverted to total reflux). In this example a reboiler with a two liter inventory and a 444 watt power input heating mantle was used at full power to generate steam for return to the column. The $(NH_2OH)_2H_2SO_4$, $H_2SO_4$ and water content of the column bottoms to the reboiler were measured by titration of a sample, and the % hydrolysis in the column calculated. These numbers, the feed ratios and the proportion of the total "acid" which was $(NH_2OH)_2H_2SO_4$ are displayed in Table 1. This latter value decreases as boil-up increases, because any other component must be water only and $H_2SO_4$; and $H_2SO_4$ is minor in amount compared to $(NH_2OH)_2H_2SO_4$ and water unless the percent hydrolysis is low.

TABLE 1

| | 444 watt | | | | |
|---|---|---|---|---|---|
| Run | A | B | C | D | E |
| Feed Rates | | | | | |
| MEKO (g/h) | 184 | 290 | 387 | 553 | 735 |
| 96% $H_2SO_4$ (g/h) | 86 | 132 | 181 | 253 | 341 |
| Column Bottoms* | | | | | |
| % $(NH_2OH_2)H_2SO_4$ | 26.7 | 33.5 | 40.8 | 45.7 | 44.1 |
| % $H_2SO_4$ | 0.29 | 0.41 | 1.73 | 3.71 | 10.3 |
| $(NH_2OH)_2H_2SO_4$ rate (g/h)** | 136 | 208 | 271 | 359 | 394 |
| % of all "acid" as $(NH_2OH)_2H_2SO_4$** | 27.2 | 34.1 | 43.7 | 52.0 | 61.4 |
| % Hydrolysis** | 98.2 | 98 | 93.3 | 88.0 | 71.9 |

*the balance was principally water with some MEKO-$H_2SO_4$
**based on $H_2SO_4$ fed and column bottoms - ignores subsequent hydrolysis in reboiler From Table 1, it is clear that some feature of the column or the reboiler restricts the percent hydrolysis such that this percentage drops at higher feed rates.

EXAMPLE 7

Example 6 was repeated at five different (and generally higher) feed rates using a twelve liter inventory reboiler and a 2000 watt power input reboiler. The results, shown in Table 2, demonstrate that similar % hydrolysis values are achievable in the same column if more heat is added to the reboiler, suggesting that boil-up was the capacity-limiting parameter in Example 6. This would be true until the boil-up was so large as to begin flooding the column.

It is believed that the factor in Example 6 restricting the percent hydrolysis is a mass transfer effect: more water favors more hydrolysis.

TABLE

| | 2000 watt | | | | |
|---|---|---|---|---|---|
| Run | A | B | C | D | E |
| Feed Rates | | | | | |
| MEKO (g/h) | 644 | 967.4 | 1476 | 2056 | 2598 |
| 96% $H_2SO_4$ (g/h) | 322.1 | 440.5 | 688.3 | 925.1 | 1147.2 |
| Column Bottoms* | | | | | |
| % $(NH_2OH_2)H_2SO_4$ | 116.9 | 23.4 | 31.8 | 34.1 | 39.0 |
| % $H_2SO_4$ | 0.61 | 0.24 | 0.99 | 1.63 | 3.39 |
| $(NH_2OH)_2H_2SO_4$ rate (g/h)** | 492.4 | 694.3 | 1010 | 1377 | 1610 |
| % of all "acid" as $(NH_2OH)_2H_2SO_4$** | 17.9 | 23.8 | 33.4 | 36.8 | 44.6 |
| % Hydrolysis** | 95(?) | 98 | 95 | 92.6 | 87.3 |

EXAMPLE 8 CONTINUOUS PROCESS WITH RECYCLE

Methyl ethyl ketoxime and 63.6 weight % $H_2SO_4$ were premixed and cooled to 50° C. before feeding to a column as described below. The column was a 30 plate nominal 2 inch (51 mm) Oldershaw column with a two liter reboiler heated by an 870 watt heating mantle operated at full power. The feed of mixture to 20th plate of the column (counted from the bottom) was 522 g/h (567 mL/h) ketone and 462 g/h (299.5 mL/h) 63.6% sulfuric acid. To the reboiler was fed a recycle stream of about 30 weight % $(NH_2OH)_2H_2SO_4$ preheated to 100° C. at a rate of about 3000 g/h (2500 mL/h).

The column was operated with the reboiler at 103° C., the 20th plate (feed plate) at 96° C. and the overhead at 74° C., with the normal 4:1 reflux ratio reverting to total reflux when the overheads temperature exceed 74.5° C.

Overheads were removed at 492 g/h and assayed 88 weight % methyl ethyl ketone, 0.13 weight % methyl ethyl ketoxime and the balance water. Samples taken of the column bottoms to the reboiler showed 97% conversion of feed acid to $(NH_2OH)_2H_2SO_4$, 3% as free acidity and 30% of all "acidity" as $(NH_2OH)_2H_2SO_4$. Samples taken of the outflow from the reboiler showed 98% conversion of fed acid and 40 weight % hydroxylammonium sulfate in the aqueous solution. Recrystallization of this aqueous solution yielded 507 g/h hydroxylammonium sulfate with 3% moisture content and the 30 weight % recycle stream described above. After drying the cake at 60° C. and 22 mm mercury pressure (3.3 kPa), it assayed as 99 weight % $(NH_2OH)_2H_2SO_4$, with essentially quantitative yield.

We claim:

1. A process for the continuous hydrolysis of a ketoxime which comprises the steps:
    (a) feeding to a fractional distillation column at an intermediate feed point a feed mixture comprising an aliphatic or cycloaliphatic ketoxime of 3–8 carbons and an inorganic acid which is not strongly oxidizing;
    (b) feeding steam to the column adjacent the base of said column;
    (c) operating said column with sufficient steam feed, sufficient effective plates between said feed point and the base of said column and sufficient reflux to hydrolyze said ketoxime in said column and form the ketone corresponding to said ketoxime and the hydroxylammonium salt of said inorganic acid;
    (d) recovering an overhead comprising said ketone; and
    (e) recovering as bottoms an aqueous solution comprising said hydroxylammonium salt.

2. The process of claim 1 wherein said aqueous solution is boiled to generate said steam and the remaining concentrated aqueous solution is continuously withdrawn.

3. The process of claim 2 wherein said concentrated aqueous solution is cooled to form hydroxylammonium salt solids and mother liquor and said hydroxylammonium salt solids are separated from said mother liquor.

4. The process of claim 3 wherein said mother liquor is combined with said aqueous solution and said combination is boiled to generate said steam.

5. The process of claim 1 or 4 wherein said column contains sufficient effective plates above said feed point and the reflux ratio is sufficient to form an overheads having an equilibrium ratio of water to ketone.

6. The process of claim 5 wherein the temperature of said overheads is continuously sensed and the column is operated at complete reflux when the temperature of said overheads exceeds by a predetermined level the boiling point of an overheads having said equilibrium ratio, and is operated with partial reflux when the temperature of said overheads is within said predetermined level of said boiling point.

7. The process of claim 1 wherein said ketoxime has 3–4 carbons.

8. The process of claim 7 wherein said ketoxime in methyl ethyl ketoxime.

9. The process of claim 7 wherein said ketoxime is acetone oxime.

10. The process of claim 1 wherein said inorganic acid is selected from the group consisting of hydrochloric, sulfuric and phosphoric acids.

11. The process of claim 10 wherein said inorganic acid is sulfuric acid.

12. The process of claim 1 wherein said column is a tray column.

13. The process of claim 1 wherein said column is a packed column.